United States Patent
Hanson

[11] Patent Number: 5,919,174
[45] Date of Patent: Jul. 6, 1999

[54] SUCTION VALVE ASSEMBLY

[75] Inventor: Sean P. Hanson, Murray, Utah

[73] Assignee: Sorenson Critical Care, Inc., Salt Lake City, Utah

[21] Appl. No.: 08/792,068

[22] Filed: Feb. 3, 1997

[51] Int. Cl.⁶ .................................................. A61M 25/00
[52] U.S. Cl. ........................ 604/283; 604/246; 604/249; 604/171; 251/320; 251/322
[58] Field of Search .................... 604/280, 283, 604/284, 246, 247–249, 905, 171, 30, 33, 236; 251/208, 320, 217, 322; 128/DIG. 12

[56] References Cited

U.S. PATENT DOCUMENTS

| | | | |
|---|---|---|---|
| 4,333,455 | 6/1982 | Bodicky | 128/214.4 |
| 4,497,468 | 2/1985 | Hubbard et al. | 251/117 |
| 4,569,344 | 2/1986 | Palmer . | |
| 4,624,662 | 11/1986 | Le | 604/249 |
| 4,767,409 | 8/1988 | Brooks | 604/171 |
| 4,836,199 | 6/1989 | Palmer | 128/207.16 |
| 4,967,743 | 11/1990 | Lambert | 128/202.16 |
| 5,220,916 | 6/1993 | Russo | 128/207.16 |
| 5,269,768 | 12/1993 | Cheung | 604/248 |
| 5,300,043 | 4/1994 | Devlin et al. | 604/250 |
| 5,325,851 | 7/1994 | Reynolds et al. | 128/207.16 |
| 5,342,326 | 8/1994 | Peppel et al. | 604/284 |
| 5,349,950 | 9/1994 | Ulrich et al. | 128/207.16 |
| 5,370,610 | 12/1994 | Reynolds | 604/43 |
| 5,433,195 | 7/1995 | Kee et al. | 128/207.14 |
| 5,460,613 | 10/1995 | Ulrich et al. | 604/118 |
| 5,490,503 | 2/1996 | Hollister | 128/205.12 |
| 5,531,712 | 7/1996 | Malcolm et al. | 604/247 |

Primary Examiner—Corrine McDermott
Assistant Examiner—Cris L. Rodriguez
Attorney, Agent, or Firm—Trask, Britt & Rossa

[57] ABSTRACT

A modular ventilating/aspirating assembly includes a catheter subassembly, including a sputum trap; an optional valved manifold and a suction control valve with an actuator oriented at an acute angle with respect to the lumen of the valve. The suction control valve includes a connection end which may couple selectively to a catheter subassembly or to other peripheral devices.

45 Claims, 4 Drawing Sheets

SUCTION VALVE ASSEMBLY

BACKGROUND OF THE INVENTION

1. Field

This invention relates generally to suction control valves. It is specifically directed to such valves in medical applications, and provides a system in which an improved such valve may be used in association with suction probes of various types, including catheter assemblies.

2. State of the Art

Suction delivery systems, particularly in a hospital or laboratory environment, typically require control valves with special capabilities. As an example, systems for endotracheal suctioning typically include a manifold enabling introduction of ventilating gases and intermittent exhalation of patient breath simultaneously with insertion and operation of a tracheal suctioning catheter. The manifold structure typically includes multiple ports, one of which is interfaced to a patient through a patient connection device of some type. The suction catheter is often included within an assembly which is connectable to a second port of the manifold. The catheter assembly conventionally includes a collapsible plastic envelope - entirely surrounding the catheter. A practitioner manually externally collapses the envelope onto the external surface of the catheter, and advances the catheter through the manifold into the throat of a patient, retracting the catheter in a similar fashion following the aspiration procedure. A suction control valve is carried by the other end of the catheter, and connects the lumen of the catheter to a vacuum source.

A suction catheter may be viewed as a special case of suction probes generally. For example, suction is also used to remove mucus and other fluids from the nasal passages and/or oral cavities of patients. A suction control valve is often used in connection with wands or other probes specifically designed for such special applications. The control valve is generally structured to have a normally closed condition which can be overcome with finger pressure applied to an actuator, such as a plunger, lever or knob. In some instances, the valve may be capable of regulating the level of suction applied, but more importantly, the valve should have a reliable biasing system to isolate the vacuum source except when a vacuum is intentionally and deliberately applied.

Various expedients have been proposed for controlling and/or regulating the application of suction through a suction catheter. U. S. Pat. No. 4,569,344 illustrates a typical arrangement in which a suction catheter is connected to a vacuum source through an aspirating vacuum control valve. The valve provides a flow channel which is axial with respect to the catheter lumen. The channel comprises oppositely directed conduits, one of which is fixed to the catheter and the other of which is connectable to a vacuum supply tube. The channel is normally sealed against flow by a resilient seal member. A valve actuator member may be pressed down, thereby moving a plunger against the normal bias of the seal member. The seal is thereby distorted, opening the catheter lumen to the vacuum source. The actuator may be turned to lock the stem into its closed position. U.S. Pat. No. 5,064,168 discloses a control valve of much simpler construction. Unlike the '344 valve, the flow path through the '168 valve is at right angles; the valve is structured to attach to a standard medical luer taper and the bias mechanism of the valve is placed out of the fluid flow path.

While previously available catheter assemblies and their associated suction control valves have been useful, they all have certain shortcomings. A permanent connection to the catheter assembly restricts use of the valve to a single purpose. Conventional orientation of the valve with respect to the lumen of the catheter, or other probe, requires actuation at right angles to the lumen. This mode of actuation is ergonomically disadvantageous for handed-handed operation. Catheter assemblies typically include relatively expensive fixtures at opposite ends. The entire assembly must be discarded with the catheter, even though a procedure which requires periodic catheter replacement may not inherently require replacement of the end fixtures.

There remains a need for a medical suction system of improved versatility and economy. There is a particular need for an integrated modular system which permits the selective discard of individual components while retaining more expensive components for continued use during a procedure or, in appropriate circumstances, multiple use. The avoidance of patient discomfort and enhanced convenience of use are also desirable objectives in the field of this invention.

SUMMARY OF THE INVENTION

The present invention provides a versatile suction control valve assembly. The invention may be viewed as a modular assembly of components adapted for use with an improved suction control valve. It may alternatively be viewed as a modular probe assembly, most often including a modular catheter assembly. In any case, the total assembly is characterized by several advantageous features, each of which is individually useful in a variety of contexts. To avoid duplicative description, the invention is described in this disclosure with particular reference to a suction catheter assembly. The individual components of the assembly are useful for other applications, particularly, but not exclusively, within patient treatment environments. In this connection, the disclosures of copending, commonly assigned U.S. patent applications Ser. Nos. 08/794,337 filed Feb. 3, 1997 (identified in the internal files of applicant and its attorneys as Case No. 3097) and (identified in the internal files of applicant and its attorneys as Case No. 3098) are incorporated by reference as though fully set forth in this disclosure.

The invention may be embodied as an assembly including a suction catheter subassembly. The subassembly typically includes a suction catheter with a first end slidably mounted through a first coupling structure and a second end carrying a second coupling structure. The first and second couplings of the catheter subassembly are usually connected by a flexible collapsible sheath which surrounds the catheter between those couplings. The first coupling may be constructed and arranged for detachable connection to a manifold component of patient interface structure. By "interface structure" is meant any apparatus connecting a patient directly or indirectly to suction, ventilation or other equipment. The second coupling may be constructed and arranged for detachable connection to a suction control valve.

Preferably, the first coupling structure includes a sputum trap, comprising a hollow chamber with a first end carrying a connector element, and a second end constructed to receive the catheter. A wiper element may be mounted within the chamber. One version of the wiper element is a resilient annular plug having a central bore which slidingly engages the exterior of the catheter. The annular plug fills the space between the catheter and the interior surface of the sputum chamber through a portion of the length of the chamber, usually adjacent the second end, such that the central bore of the plug constitutes an entry port for the catheter. As the catheter is moved reciprocally through the sputum trap, the wiper element constitutes means for wiping the exterior surface of the catheter as it is withdrawn through the sputum trap. Fluids are collected in the portion of the trap not occupied by the plug. These collected wastes are normally discarded along with the catheter subassembly.

Besides the catheter subassembly, the assembly of this invention further may include a suction control valve having a connection end. That end may carry structure mutually adapted with the second coupling of the catheter subassembly to effect a detachable fluid flow connection between a lumen of the catheter and a vacuum source through a lumen of the valve. The valve may take various forms, but typically includes a supply member, which includes a vacuum source end and the connection end of the valve. A stem member intersects the supply member, thereby creating an open communication between these members. The stem member houses a valve stem assembly, which carries actuator structure accessible from outside the valve. The stem member ideally intersects the supply member at an acute angle of intersection oriented towards the connection end. The valve stem may be selected from a variety of designs, but the plunger type is presently preferred.

A preferred valve stem assembly includes a plunger oriented for reciprocal movement within the stem member between a normally closed position in which the plunger blocks flow through the supply member and an open position in which an open portion of the stem is brought into registration with said supply member, whereby to permit fluid flow through the supply member. By "open portion" is meant a reduced diameter, a passageway or any other structural expedient which permits flow past or through the stem. A biasing spring may be arranged to urge the plunger to its normally closed position. The actuator is structured to react to downward thumb pressure, whereby to move the plunger against the spring from its normally closed position to its open position. The valve stem and actuator may be cooperatively adapted such that either may be rotated to a locked condition in the closed position.

Because the suction valve is readily detached from the catheter subassembly, the complete assembly may include peripheral components, such as suction probes, adapted to couple with the connection end of the valve. An assembly may also include one or more manifold structures. In some instances, a complete assembly may include a plurality of catheter subassemblies, of either identical or different constructions.

BRIEF DESCRIPTION OF THE DRAWINGS

In the drawings, which illustrate what is currently regarded as the best mode for carrying out the invention.

DETAILED DESCRIPTION OF THE ILLUSTRATED EMBODIMENT

Figure 1:
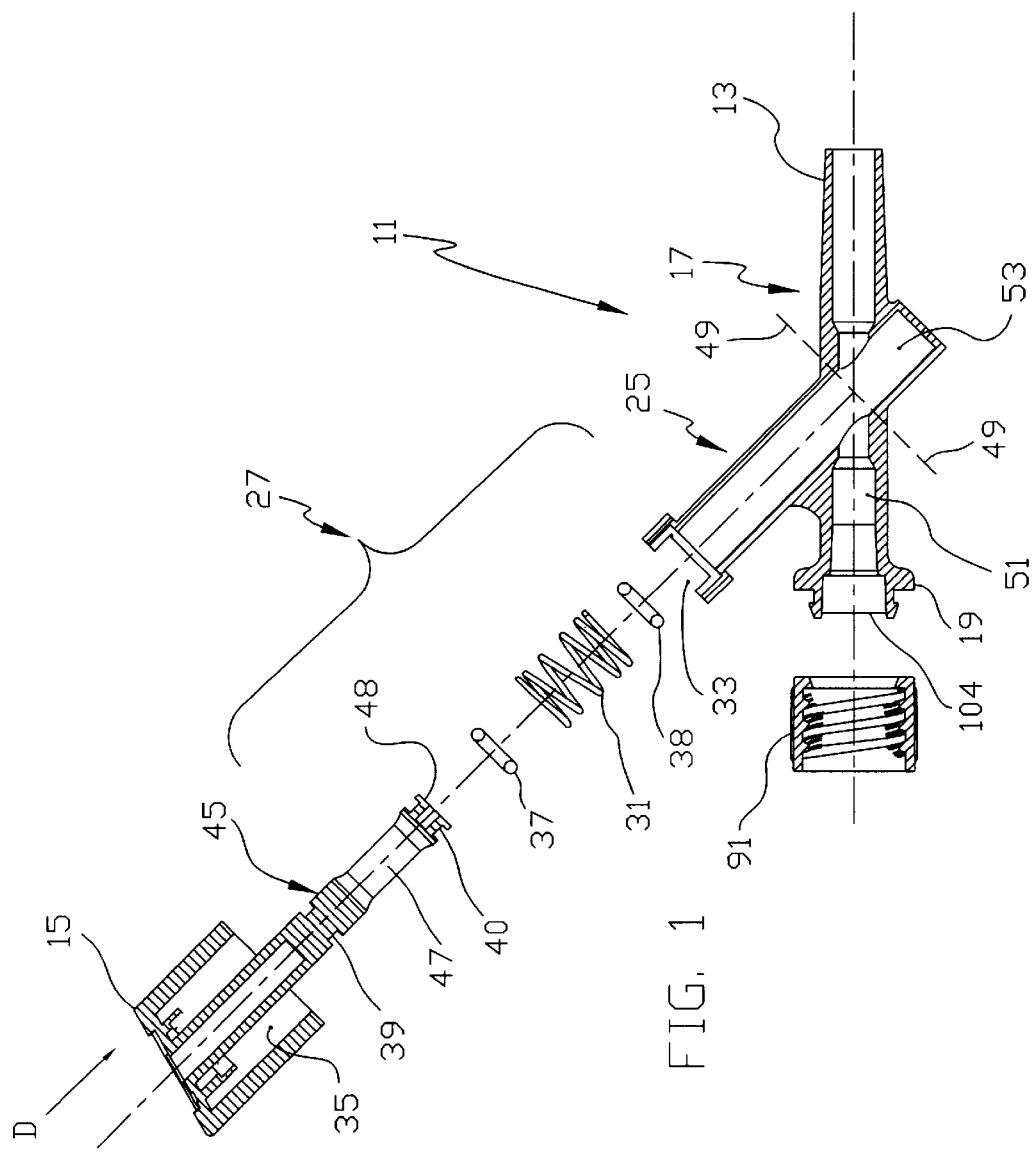
FIG. 1 is an exploded view in cross section of a suction control valve of this invention.

An erganomically advantageous suction control valve, designated generally 11, of this invention includes a tapered end 13 sized appropriately for connection to a standard flexible vacuum hose or tube (not shown). Ideally, the end 13 is an approximately cylindrical conduit with an outer surface configured as a standard medical luer taper. In use, when the valve 11 is grasped by the hand, the thumb is inevitably positioned over an actuator cap 15. As illustrated, the valve 11 includes a first (supply) member, generally 17, which carries the tapered (source) end 13 and a connection end 19. A second (stem) member, generally 25, intersects the first member 17, carries the actuator cap 15, and houses a plunger assembly, generally 27, as best shown by FIG. 1. The stem member 25 intersects the supply member 17 to define an acute angle of intersection of approximately 45 (typically between about 35 and about 85) degrees, oriented towards the connection end 19. Angles of intersection outside this range, while operable, are generally less comfortable for the operator attempting single-handed suction control.

Referring to FIG. 1, a compression spring 31 is positioned within the cap 15, being retained within the spring socket 33 and the cap cavity 35. "O"-ring seals 37, 38 are retained within respective annular grooves 39, 40 in a plunger stem, generally 45. The stem 45 is an approximately cylindrical member with a channel 47 located between the seals 37, 38. In the normal closed condition, biased by the spring 31, the stem end 48 and seal 38 are positioned approximately at the plane 49, thereby sealing the valve lumen 51 against flow induced by a vacuum source (not shown) connected to the end 13. When the actuator cap 15 is pressed down, typically by thumb pressure, in the direction indicated D, the stem end 48 is moved into the well 53, thereby bringing the channel 47 into registration with the lumen 51. The rate of flow permitted by the valve 11 can be controlled to some extent by adjusting the distance that the stem 45 is depressed; that is, the extent to which the channel 47 overlaps the lumen 51. Release of thumb pressure permits the spring 31 to urge the stem 45 upward, opposite direction D, to reseal the lumen 51.

Figure 2:
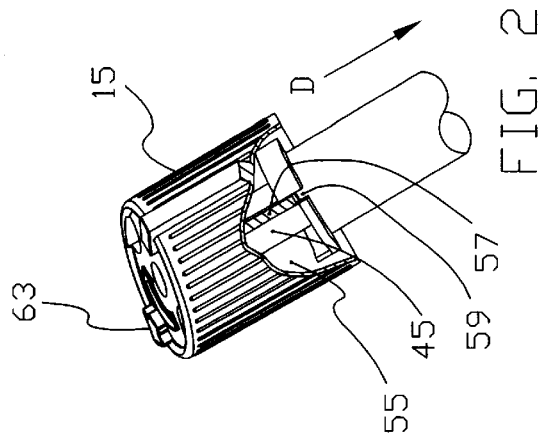
FIGS. 2 and 3 are fragmentary views, partially broken away, of a portion of the valve of FIG. 1.
Figure 3:
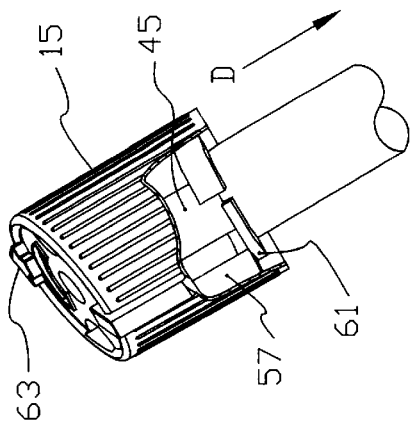

The cap 15 may be rotated, as shown by FIGS. 2 and 3, between locked and unlocked conditions. The internal surface 55 of the cap 15 carries rails 57. In normal use position (FIG. 2), each rail 57 registers with accommodation slots 59 so that the plunger 45 is free to travel downward in direction D. The cap 15 may be rotated to the position shown by FIG. 3 so that the rails 57 register with stop plates 61. As so positioned, the plunger stem 45 is locked against downward movement. An arrow 63 on the upper surface of the cap 15 indicates the orientation of the channel 47, and thus the open or closed condition of the valve 11

Figure 4:
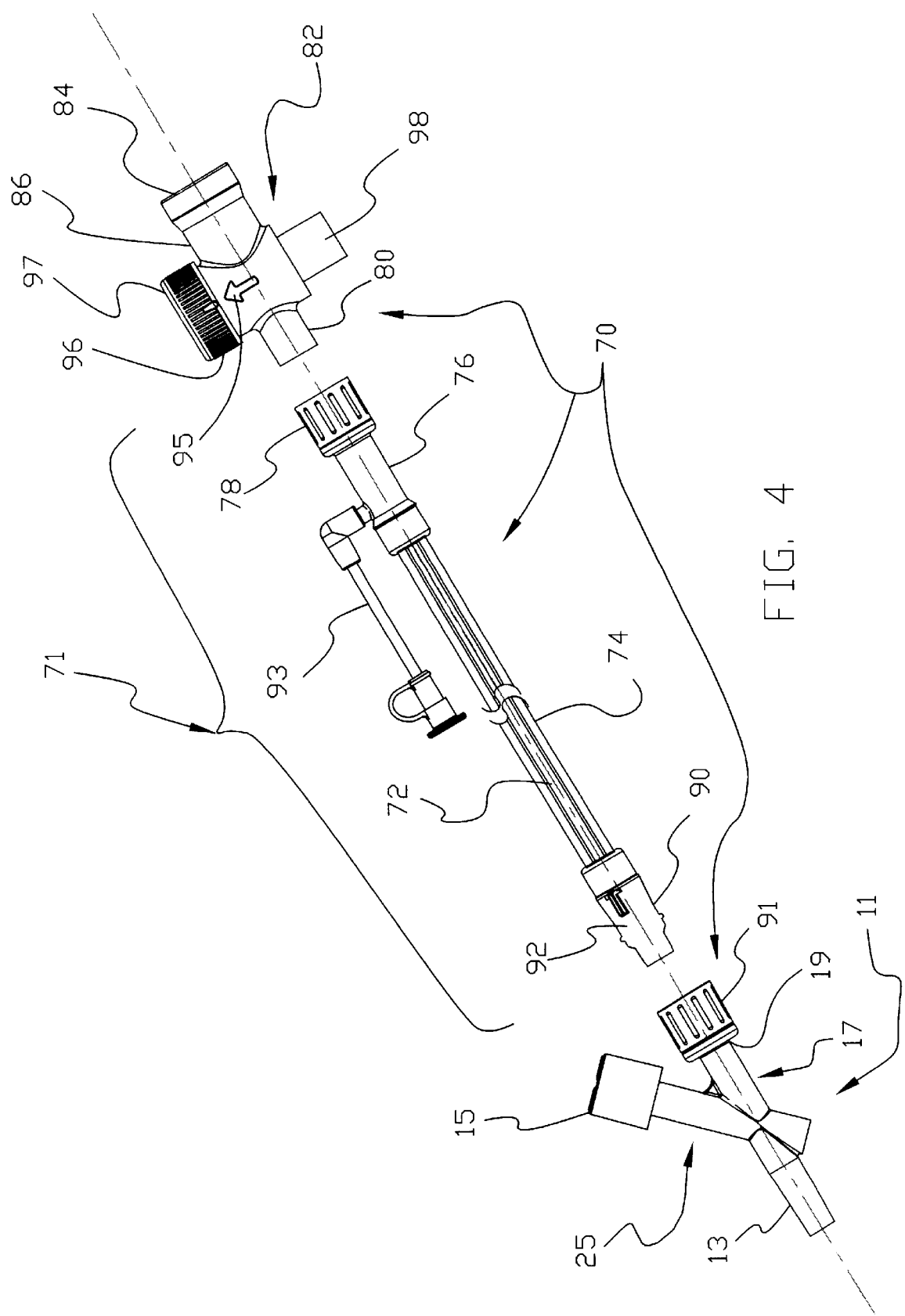
FIG. 4 is an exploded plan view, partially broken away, illustrating the valve of FIG. 1 in operable association with components of a suction catheter assembly.
Figure 5:
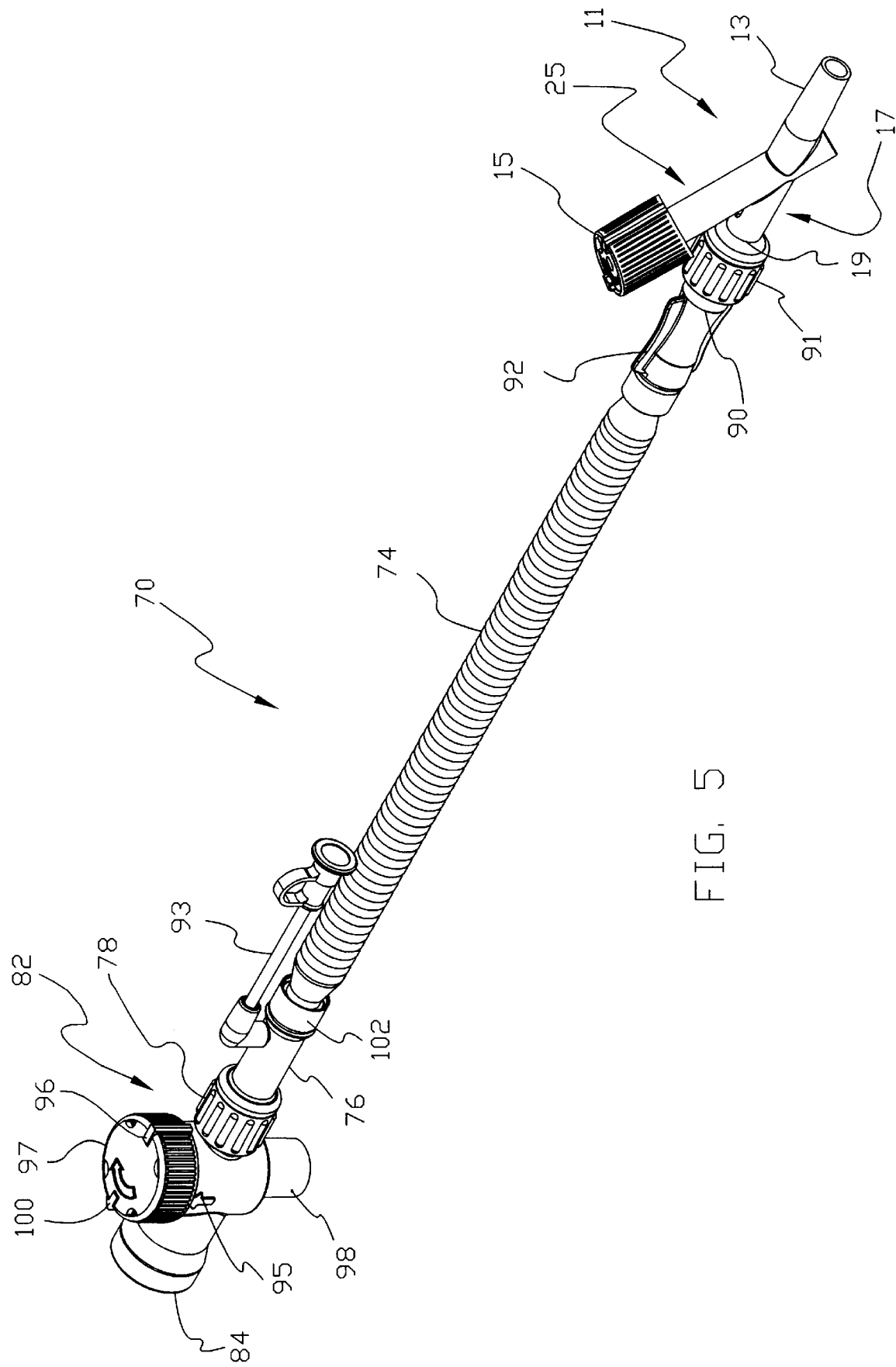
FIG. 5 is a perspective view of the assembly of FIG. 4, in fully assembled condition and rotated to expose features not visible in FIG. 4.

Referring to FIGS. 4 and 5, a valve 11 of this invention is shown in association with other components of a ventilating/aspirating assembly, designated generally 70. A suction catheter subassembly, generally 71, includes a suction catheter 72 carried within a flexible sheath 74. The catheter 72 may be selectively extended or withdrawn (by manual manipulation through the sheath) through a sputum trap 76, which is in turn connected by a luer collar 78 to an access port 80 of a valved manifold, generally 82. A swivel connector 84 is carried by a patient connection port conduit 86 of the valved manifold 82. The valued manifold 82 and swivel connector 84 are preferably constructed as described in greater detail in Ser. Nos. 08/794,337, filed Feb. 3,1997 and 08/792,062, filed Feb. 3,1997, previously incorporated by reference into this disclosure.

The suction control valve 11 is connected to the distal end 90 of the catheter 72 by means of a luer collar 91 and wing connector 92. An irrigation access tube 93 extends from the sputum trap 76. An arrow 95 registers with a witness mark 96 carried by the valve knob 97 to indicate the open/closed status of the valved manifold 82. In the open condition of the manifold, the catheter 72 may be manipulated through the valved manifold 82 and the connector 84 into a patient intubation fixture (not shown). The system is then sealed against leakage of respiration gases passing into the manifold ventilator port by sealing structure within the sputum trap 76. With the catheter 72 withdrawn, the knob 97 may be turned to closed condition. The luer collar 78 may then be turned to release the catheter subassembly 71 from its connection to the valved manifold 82. Aspiration/ventilation may then continue through the patient connection 86 and ventilator ports 98. As best shown by FIG. 5, an arrow 100 on the upper surface of the knob 97 indicates the open valved manifold condition. FIG. 4 shows the valve 82 in its closed condition.

A significant benefit of the catheter subassembly 71 illustrated is the provision of the sputum trap 76. This component collects excretions remote from the valved manifold 82, and can be discarded with the catheter 72. Alternatively, a coupling 102 may be provided so that the sputum trap 76 may periodically be replaced. The catheter 72 may be withdrawn into its sheath 74. The valve knob 97 is then turned to a closed condition. The trap 76 is then decoupled at the luer collar 78 and coupling 102, and a fresh trap installed. The knob 97 is then turned to its open condition and the catheter 72 urged back into its suctioning position.

The luer collars 78, 91 permit discard and replacement of the sputum trap 76, catheter 72 and sheath 74 components of the subassembly 71, while salvaging the more expensive valve components 11, 82, either for continued use in an ongoing procedure or for subsequent use in other procedures. For example, the suction valve 11 may be disconnected occasionally at the luer collar 91 and connected to a wand or other suitable suction probe for intermittent suctioning tasks required by the patient utilizing the assembly 70. Other procedures, notably ongoing ventilation, can be effected through the manifold when the assembly 70 is disconnected at the collar 78. The valved manifold 82 will normally be in its closed condition under those circumstances, but the open condition affords access for the introduction of medicaments or other appliances as needed.

Either the suction valve 11 or the valved manifold assembly 82 may be interfaced with catheter subassemblies other than that illustrated 71. For example as illustrated by FIG. 1, the entry 104 to the first member 17 is constructed with stepped diameters selected to register with standard tubing diameters. Alternatively, this entry 104 may be provided as a gradually tapering cone to accommodate tubes of different diameters. Generally, the connection end 19 is structured to accept tubings of various standard diameters in plug fit association. In other cases, adapters may be provided to interface various tubes or probes to the luer collar 91 or entry 104. In any case, the valve 11 may readily be adapted to catheters and other peripheral devices, notably suction probes, supplied from a variety of vendors. Similar structural provisions may be made at the access port 80 of the manifold 82 to interface with a variety of catheters and peripheral devices.

While the valve structure 11 illustrated is highly preferred, it is within contemplation that other valve structures, such as of the "stop cock" or "trumpet" variety, could be substituted in an assembly 70. The luer collar attachment mechanism or similar decoupling arrangement should be provided at the connection end 19 to preserve the advantage of modular construction. The valve components 11, 82 may be disposable, or they may be constructed of materials suitable for sterilization or disinfection procedures.

Figure 6:
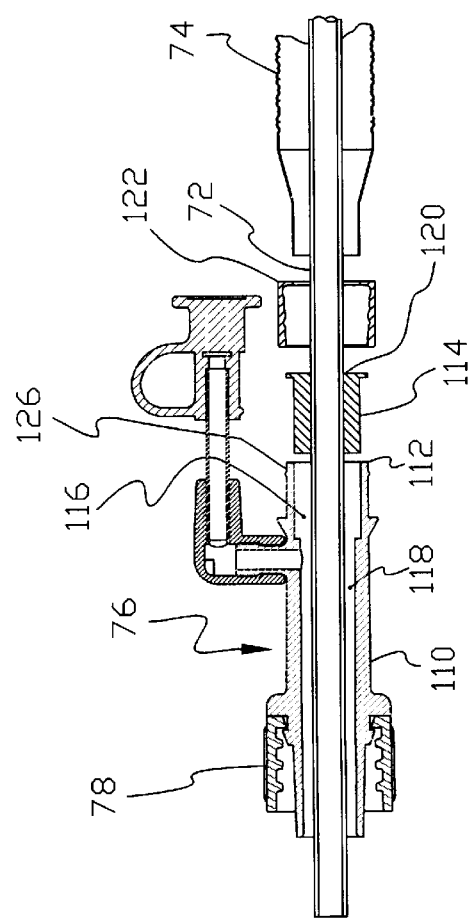
FIG. 6 is an exploded in cross-section view of the sputum trap component of FIGS. 4 and 5.

A presently preferred construction of the sputum trap 76 is illustrated by FIG. 6. As shown, the trap 76 comprises a hollow chamber 110 with a first end carrying a luer collar 78 and a second end 112 constructed to receive a catheter 72. A wiper element 114 is mounted within the chamber 110, at its end 112, occupying a significant, but minor, portion 116 of the chamber interior 118. The illustrated wiper element is a resilient annular plug having a central bore 120 which firmly engages the exterior of the catheter 72 in sliding relationship. The central bore 120 constitutes an entry port for the catheter 72. As the catheter 72 is moved reciprocally through the sputum trap 76, the wiper element 114 squeegees sputum and similar substances from the outer surface of the catheter 72, the removed substances being collected in the interior chamber 118 of the chamber 110 not occupied by the plug-like wiper element 114. In assembled condition, a retainer cap 122 clamps the sheath 74 against the outer surface 126 of the end 112 and retains the wiper element 114 within its assigned portion 116 of the chamber 110 as the catheter 72 is advanced or withdrawn through the trap 76.

Figure 7:
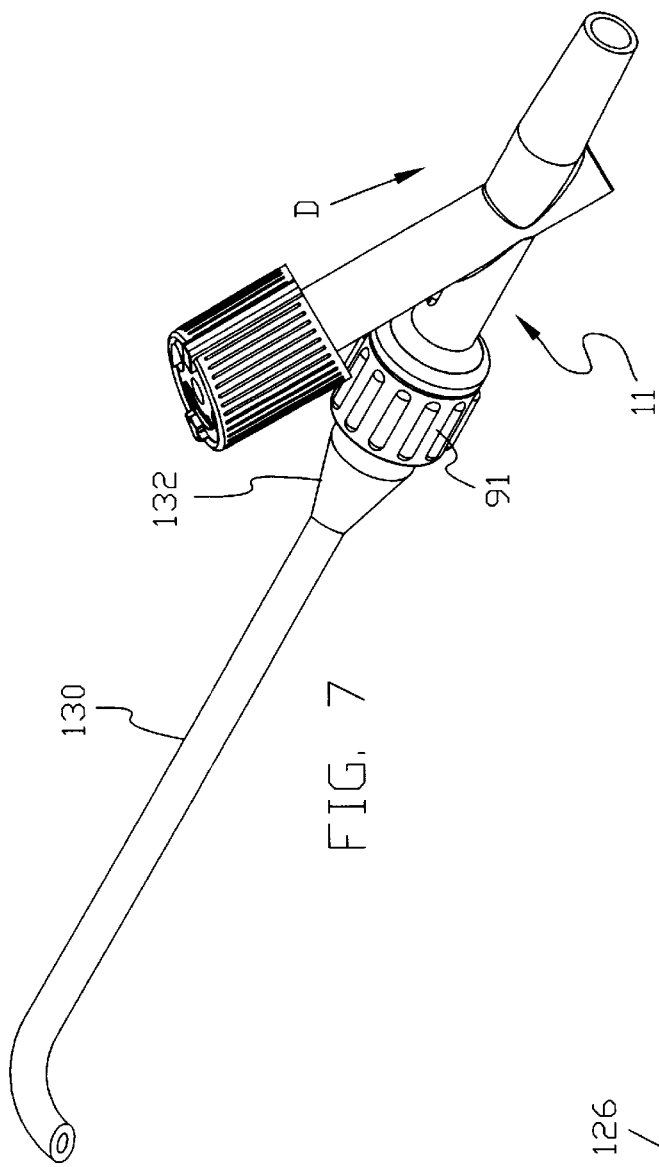
FIG. 7 is a plan view of a typical peripheral suction probe of the invention.

FIG. 7 illustrates a typical peripheral suction wand 130 with an end fitting structured to mate with the luer collar 91 of the valve 11 in place of a catheter subassembly 71.

Reference in this disclosure to details of the illustrated or other preferred embodiments is not intended to limit the scope of the appended claims, which themselves recite those features regarded as important to the invention.

What is claimed is:

1. A suction catheter assembly, comprising:
   a suction catheter with a first end slidably mounted through a first coupling structure and a second end carrying a second coupling structure;
   said first coupling structure being constructed and arranged for detachable connection to a manifold component of a patient interface structure; and
   said second coupling structure being constructed and arranged for connection to a suction control valve.

2. The assembly according to claim 1, wherein said first and second coupling structures are connected by a flexible collapsible sheath which surrounds said suction catheter between said first and second coupling structures.

3. The assembly according to claim 1, further including a suction control valve having a connection end carrying structure mutually adapted with said second coupling structure to effect a detachable fluid flow connection between a lumen of said suction catheter and a vacuum source through a lumen of said suction control valve.

4. The assembly according to claim 3, wherein said first and second coupling structures are connected by a flexible collapsible sheath which surrounds said suction catheter between said first and second coupling structures.

5. The assembly according to claim 3, wherein said suction control valve comprises:
   a supply member, which includes a vacuum source end and said connection end; and
   a stem member, which:
      intersects said supply member,
      carries actuator structure, and
      houses a valve stem assembly;
   said stem member intersecting said supply member at an acute angle of intersection oriented towards said connection end.

6. The assembly according to claim 5, wherein said valve stem assembly is a plunger assembly.

7. The assembly according to claim 5, wherein said acute angle is between about 35 and about 85 degrees.

8. The assembly according to claim 3, further including a suction probe adapted to couple with said connection end of said valve.

9. A suction catheter assembly according to claim 1, including a suction control valve, comprising:
 a supply member, which includes a vacuum source end and a connection end;
 a stem member, which intersects said supply member and houses a valve stem assembly, including actuator structure accessible from outside said suction control valve; and
 said stem member intersecting said supply member at an acute angle of intersection oriented towards said connection end.

10. A suction catheter assembly according to claim 9, wherein said valve stem assembly includes a plunger oriented for reciprocal movement within said stem member between:
 a normally closed position in which said plunger blocks fluid flow through said supply member; and
 an open position in which said plunger is brought into registration with said supply member, whereby to permit fluid flow through said supply member.

11. A suction catheter assembly according to claim 10, including a biasing spring arranged to urge said plunger to its normally closed position.

12. A suction catheter assembly according to claim 11 wherein said actuator structure is structured to react to downward thumb pressure, whereby to move said plunger against said spring from its normally closed position to its open position.

13. A suction catheter assembly according to claim 9, wherein said acute angle is between about 35 and about 85 degrees.

14. A suction catheter assembly, comprising:
 a suction catheter with a first end slidably mounted through a first coupling structure and a second end carrying a second coupling structure;
 said first coupling structure being constructed and arranged for detachable connection to a manifold component of a patient interface structure; and
 said second coupling structure being constructed and arranged for connection to a suction control valve, wherein said first coupling structure includes a sputum trap, comprising:
 a hollow chamber with:
 a first end carrying a connector element, and
 a second end constructed to receive said suction catheter; and
 a wiper element having a central bore which slidingly engages the exterior of said suction catheter as said suction catheter is moved reciprocally through said sputum trap, said wiper element constituting means for wiping the exterior surface of said suction catheter as it is withdrawn through said sputum trap.

15. The assembly according to claim 14, wherein said wiper element is structured to effect a seal against the exterior surface of said suction catheter.

16. The assembly according to claim 2, wherein said first and second coupling structures are connected by a flexible collapsible sheath which surrounds said suction catheter between said first and second coupling structures.

17. The assembly according to claim 16, wherein said wiper element is structured to effect a seal against the exterior surface of said suction catheter.

18. The assembly according to claim 3, wherein;
 said suction control valve further having a connection end carrying structure mutually adapted with said second coupling structure to effect a detachable fluid flow connection between a lumen of said suction catheter and a vacuum source through a lumen of said suction control valve, and
 said wiper element is mounted within said sputum trap hollow chamber.

19. The assembly according to claim 18, wherein said wiper element comprises a resilient annular plug.

20. The assembly according to claim 4, wherein said first and second coupling structures are connected by a flexible collapsible sheath which surrounds said suction catheter between said first and second coupling structures.

21. The assembly according to claim 20, wherein said wiper element comprises a resilient annular plug.

22. The assembly according to claim 14, wherein said wiper element is positioned with respect to said hollow chamber such that a substance removed from the exterior surface of said suction catheter as said suction catheter is withdrawn through said sputum trap is collected within said hollow chamber.

23. The assembly according to claim 22, wherein said wiper element is structured to effect a seal against the exterior surface of said suction catheter.

24. The assembly according to claim 22, wherein said wiper element is mounted within said hollow chamber.

25. The assembly according to claim 24, wherein said wiper element comprises an annular plug.

26. The assembly according to claim 25, wherein said annular plug is structured to effect a seal against the exterior surface of said suction catheter.

27. The assembly according to claim 26, wherein said annular plug is resilient.

28. A suction catheter assembly, comprising:
 a suction catheter with a first end slidably mounted through a first coupling structure and a second end carrying a second coupling structure;
 said first coupling structure being constructed and arranged for detachable connection to a manifold component of a patient interface structure; and
 said second coupling structure being constructed and arranged for connection to a suction control valve, and including a suction control valve, comprising:
 a supply member, which includes a vacuum source end and a connection end; and
 a stem member, which intersects said supply member and houses a valve stem assembly, including actuator structure accessible from outside said suction control valve;
 said stem member intersecting said supply member at an acute angle of intersection oriented towards said connection end wherein said connection end is structured to accept tubings of various standard diameters in plug fit association.

29. A vacuum probe assembly, including:
 a suction control valve, comprising:
 a supply member, which includes a vacuum source end and a connection end; and
 actuation means operable selectively to open said supply member, whereby to apply vacuum at said connection end, and to close said supply member whereby to prevent application of vacuum at said connection end;

said connection end being structured releasably and interchangeably to connect to various vacuum probes; and a selection of vacuum probes.

30. The assembly according to claim 29, wherein said selection of vacuum probes includes a catheter subassembly.

31. The assembly according to claim 30, wherein said suction control valve comprises:

a supply member, which includes a vacuum source end and a connection end; and a stem member, which intersects said supply member and houses a valve stem assembly, including actuator structure accessible from outside said suction control valve.

32. The assembly according to claim 31, wherein said valve stem assembly includes a plunger oriented for reciprocal movement within said stem member between:

a normally closed position in which said plunger blocks flow through said supply member; and an open position in which said plunger is brought into registration with said supply member, whereby to permit fluid flow through said supply member.

33. The assembly according to claim 32, including a biasing spring arranged to urge said plunger to its normally closed position.

34. The assembly according to claim 33, wherein said actuator is structured to react to downward thumb pressure, whereby to move said plunger against said spring from its normally closed position to its open position.

35. The assembly according to claim 31, wherein said stem member intersects said supply member at an acute angle of intersection oriented towards said connection end.

36. The assembly according to claim 35, wherein said acute angle is between about 35 and about 85 degrees.

37. The assembly according to claim 30, wherein said catheter subassembly, comprises:

a suction catheter with a first end slidably mounted through a first coupling structure and a second end carrying a second coupling structure;

said first coupling being constructed and arranged for detachable connection to a manifold component of patient interface structure; and said second coupling being constructed and arranged for connection to said suction control valve.

38. A vacuum probe assembly, including:

a suction control valve, comprising:

a supply member, which includes a vacuum source end and a connection end; and actuation means operable selectively to open said supply member, whereby to apply vacuum at said connection end;

said connection end being structured releasably and interchangeably to connect to various vacuum probes; and a selection of vacuum probes wherein said selection of vacuum probes includes a catheter subassembly; and a stem member, which intersects said supply member and houses a valve stem assembly including actuator structure accessible from outside said suction control valve wherein said connection end is structured to accept tubings of various standard diameters in plug fit association.

39. A vacuum probe assembly, including:

a suction control valve comprising:

a supply member, which includes a vacuum source end and a connection end; and actuation means operable selectively to open said supply member, whereby to apply vacuum at said connection end;

said connection end being structured releasably and interchangeably to connect to various vacuum probes; and a selection of vacuum probes; wherein said selection of vacuum probes includes a catheter subassembly comprising:

a suction catheter with a first end slidably mounted through a first coupling structure and a second end carrying a second coupling structure;

said first coupling being constructed and arranged for detachable connection to a manifold component of patient interface structure; and said second coupling being constructed and arranged for connection to said suction control valve, and wherein said first coupling structure includes a sputum trap, comprising:

a hollow chamber with:

a first end carrying a connector element, and a second end constructed to receive said suction catheter; and a wiper element having a central bore which slidingly engages the exterior of said suction catheter as said suction catheter is moved reciprocally through said sputum trap, said wiper element constituting means for wiping the exterior surface of said suction catheter as it is withdrawn through said sputum trap.

40. The assembly according to claim 39, wherein said wiper element is positioned with respect to said hollow chamber such that a substance removed from the exterior surface of said suction catheter as said catheter is withdrawn through said sputum trap is collected within said hollow chamber.

41. The assembly according to claim 40, wherein said wiper element is structured to effect a seal against the exterior surface of said suction catheter.

42. The assembly according to claim 40, wherein said wiper element is mounted within said chamber.

43. The assembly according to claim 42, wherein said wiper element comprises an annular plug.

44. The assembly according to claim 43, wherein said annular plug is structured to effect a seal against the exterior surface of said suction catheter.

45. The assembly according to claim 44, wherein said annular plug is resilient.

* * * * *

UNITED STATES PATENT AND TRADEMARK OFFICE
CERTIFICATE OF CORRECTION

PATENT NO.   : 5,919,174
DATED        : July 6, 1999
INVENTOR(S)  : Hanson

It is certified that error appears in the above-identified patent and that said Letters Patent is hereby corrected as shown below:

Title page,
Item [56], References Cited, U.S. PATENT DOCUMENTS, after first entry, insert -- 5,064,168     11/1991     Raines et al. --;

Column 2,
Line 6, change "handed-handed" to -- single-handed --;
Line 37, change "applications" to -- application --;
Line 38, delete entire line;
Line 39, delete entire line except -- and --; and after "and" insert -- 08/792,067 filed Feb. 3, 1997 --;
Line 40, delete entire line up to and including "3098)";

Column 3,
Line 60, change "exploded in cross-section view" to -- exploded view in cross-section --;
Line 66, change "erganomically" to -- ergonomically --;

Column 4,
Line 42, after "plunger" insert -- stem --;
Line 48, after "11" insert -- . --;
Line 59, change "valued" to -- valved --;
Lines 61 and 62, change "3,1997" to -- 3, 1997 --;

Column 5,
Line 4, after "the" insert -- swivel --;
Line 8, before "knob 97" insert -- valve --;
Line 9, after "to" insert -- a --.
Line 15, change "valved manifold condition." to -- valve condition. --; and change "valve 82" to -- valved manifold 82 --;

Column 6,
Line 25, after "end fitting" insert -- 132 --.

Column 7,
Line 61, change "claim 2," to -- claim 14, --;

UNITED STATES PATENT AND TRADEMARK OFFICE
CERTIFICATE OF CORRECTION

PATENT NO. : 5,919,174
DATED : July 6, 1999
INVENTOR(S) : Hanson

It is certified that error appears in the above-identified patent and that said Letters Patent is hereby corrected as shown below:

Column 8,
Line 1, change "claim 3," to -- claim 14, --;
Line 1, after "wherein" change ";" to -- : --;
Line 12, change "claim 4," to -- claim 18, --;

Column 10,
Line 6, after "valve" insert -- , --;
Lines 21 and 24, after "coupling" insert -- structure --.

Signed and Sealed this

Eighth Day of July, 2003

JAMES E. ROGAN
*Director of the United States Patent and Trademark Office*